(12) United States Patent
Otsuki (10) Patent No.: US 10,161,286 B2
(45) Date of Patent: Dec. 25, 2018

(54) EXHAUST GAS SAMPLING APPARATUS AND EXHAUST GAS ANALYSIS SYSTEM

(71) Applicant: HORIBA, Ltd., Kyoto (JP)

(72) Inventor: Yoshinori Otsuki, Kyoto (JP)

(73) Assignee: Horiba, Ltd., Kyoto (JP)

( * ) Notice: Subject to any disclaimer, the term of this patent is extended or adjusted under 35 U.S.C. 154(b) by 305 days.

(21) Appl. No.: 15/074,989

(22) Filed: Mar. 18, 2016

(65) Prior Publication Data

US 2016/0273438 A1 Sep. 22, 2016

(30) Foreign Application Priority Data

Mar. 20, 2015 (JP) .................................. 2015-058695

(51) Int. Cl.
| | | |
|---|---|---|
| *F01N 9/00* | (2006.01) | |
| *F01N 11/00* | (2006.01) | |
| *F01N 3/05* | (2006.01) | |
| *F01N 3/021* | (2006.01) | |
| *G01M 15/10* | (2006.01) | |

(Continued)

(52) U.S. Cl.
CPC ............ *F01N 11/007* (2013.01); *F01N 3/021* (2013.01); *F01N 3/05* (2013.01); *F01N 9/00* (2013.01); *G01M 15/102* (2013.01); *G01N 1/2205* (2013.01); *G01N 1/2252* (2013.01); *G01N 15/06* (2013.01); *F01N 2550/14* (2013.01);

(Continued)

(58) Field of Classification Search
None
See application file for complete search history.

(56) References Cited

U.S. PATENT DOCUMENTS

| | | | |
|---|---|---|---|
| 4,015,628 A | 4/1977 | Randolph | |
| 5,907,108 A * | 5/1999 | Garcia-Rubio | .......... G01N 1/38 73/28.01 |

(Continued)

FOREIGN PATENT DOCUMENTS

| | | |
|---|---|---|
| JP | 2000028499 A | 1/2000 |
| JP | 3054514 B | 6/2000 |

(Continued)

OTHER PUBLICATIONS

European Search Report for European Application No. EP 16161012.6, dated Sep. 2, 2016, 11 Pages.

(Continued)

*Primary Examiner* — Peter J Macchiarolo
*Assistant Examiner* — Jermaine L Jenkins
(74) *Attorney, Agent, or Firm* — Brooks Kushman P.C.

(57) ABSTRACT

In order to provide an exhaust gas sampling apparatus that makes it possible to simplify the entire system using a simple structure flow rate control mechanism having a small variable flow rate range as well as making the accuracy of an exhaust gas dilution ratio higher than before, the exhaust gas sampling apparatus is configured as an exhaust gas sampling apparatus that makes a multistage dilution. In addition, the exhaust gas sampling apparatus is configured to, given that a dilution ratio determined by an n-th diluter in a dilution flow path at an n-th stage as a final stage is R, make dilution ratios determined by diluters in dilution flow paths at the respective stages other than the n-th stage as the final stage substantially equal to (R+1).

11 Claims, 3 Drawing Sheets

(51) Int. Cl.
G01N 15/06 (2006.01)
G01N 1/22 (2006.01)
G01N 15/00 (2006.01)

(52) U.S. Cl.
CPC .............. *G01N 2001/2255* (2013.01); *G01N 2001/2264* (2013.01); *G01N 2015/0046* (2013.01)

(56) References Cited

U.S. PATENT DOCUMENTS

| | | | | |
|---|---|---|---|---|
| 6,200,819 | B1 * | 3/2001 | Harvey | G01N 1/2252 |
| | | | | 422/83 |
| 6,729,195 | B2 * | 5/2004 | Graze, Jr. | G01N 1/38 |
| | | | | 73/863.03 |
| 6,823,268 | B2 * | 11/2004 | Silvis | G01F 25/0053 |
| | | | | 702/30 |
| 9,389,152 | B2 * | 7/2016 | Kumagai | G01N 1/2252 |
| 2002/0166390 | A1 | 11/2002 | Graze, Jr. | |

FOREIGN PATENT DOCUMENTS

| | | |
|---|---|---|
| JP | 2013-061167 A | 4/2013 |
| WO | 97/12221 A | 4/1997 |

OTHER PUBLICATIONS

Office Action dated Sep. 18, 2018 issued for Japanese Patent Application No. 2015-058695, 7 pgs.

* cited by examiner

FIG. 3

EXHAUST GAS SAMPLING APPARATUS AND EXHAUST GAS ANALYSIS SYSTEM

CROSS-REFERENCE TO RELATED APPLICATION

This application claims priority to JP Application No. 2015-058695, filed Mar. 20, 2015, the disclosure of which is incorporated in its entirety by reference herein.

TECHNICAL FIELD

The present invention relates to an exhaust gas sampling apparatus that includes a multistage dilution flow path to dilute exhaust gas through multistage dilution.

BACKGROUND ART

For example, when measuring the amount of particulate matter (hereinafter also referred to as PM) having a predetermined particle size contained in exhaust gas, the exhaust gas is diluted at a large dilution ratio, and the diluted exhaust gas is passed through a filter at a predetermined flow rate.

As a dilution ratio is increased, an error in flow rate of dilution air flowing into a diluter, and/or an error in flow rate of exhaust gas got by the diluter become more likely to affect the accuracy of the dilution ratio. For this reason, as a dilution ratio is increased, it becomes more difficult for an exhaust gas sampling apparatus including only a single-stage dilution flow path to dilute exhaust gas with a predetermined accuracy.

In order to solve such a problem, as disclosed in Japanese Patent No. 3054514, there has been proposed an exhaust gas sampling apparatus including a two-stage dilution flow path. This exhaust gas sampling apparatus is configured to dilute exhaust gas at a dilution ratio R1 in a first stage dilution flow path, and in a second stage dilution flow path, get a part of the diluted exhaust gas resulting from the dilution in the first flow path to further dilute it at a dilution ratio R2. Each of the dilution flow paths is provided with: a dilution air flow rate controller adapted to control the flow rate of inflow dilution air; and a diluted exhaust gas flow rate controller adapted to control the flow rate of outflow diluted exhaust gas. That is, the exhaust gas sampling apparatus dilutes the exhaust gas at a desired dilution ratio R by controlling the four flow rates using the four flow rate controllers in total, respectively.

However, in the exhaust gas sampling apparatus described in Japanese Patent No. 3054514, when changing a final dilution ratio R, the flow rates to be controlled by all the four flow rate controllers have been changed so as to accurately dilute the exhaust gas. In addition, in order to respond to various dilution ratios, it has been considered that variable flow rate ranges of the respective flow rate controllers must be set to be large, thus causing increases in size and complexity of a system.

Further, as a result of intensive examination by the present inventor, the inventor has first found that an exhaust gas sampling apparatus of a multistage dilution type can make the accuracy of a final stage dilution ratio higher than before while simplifying a system configuration.

SUMMARY OF INVENTION

Technical Problem

The present invention has been made in consideration of the problems as described above, and intends to provide an exhaust gas sampling apparatus that makes it possible to simplify the entire system using a simple configuration flow rate control mechanism having a small variable flow rate range as well as improving the accuracy of an exhaust gas dilution ratio more than before.

Solution to Problem

That is, the exhaust gas sampling apparatus of the present invention is one including an n-stage dilution flow path (n is a natural number equal to or more than 2), in which a dilution flow path at a k-th stage (k is a natural number from 1 to n) is provided with: a k-th sampling pipe adapted to get exhaust gas or diluted exhaust gas resulting from dilution in a dilution flow path at a (k−1)-th stage; a k-th diluter adapted to dilute with dilution air the exhaust gas or the diluted exhaust gas got through the k-th sampling pipe; a k-th dilution air flow rate control mechanism adapted to control a flow rate of the dilution air flowing into the k-th diluter; and a k-th diluted exhaust gas flow rate control mechanism adapted to control a flow rate of diluted exhaust gas flowing out of the k-th diluter. In addition, the exhaust gas sampling apparatus is configured such that, in the dilution flow paths at the respective stages, flow rates of the exhaust gas and the diluted exhaust gases got through corresponding sampling pipes are controlled in conjunction with a flow rate of the dilution air flowing into the n-th diluter through the dilution air flow rate control mechanism at the n-th stage as a final stage.

Also, an exhaust gas dilution method according to the present invention is one using an exhaust gas sampling apparatus including an n-stage dilution flow path (n is a natural number uniformly equal to or more than 2), in which the exhaust gas sampling apparatus is an apparatus of which a dilution flow path at a k-th stage (k is a natural number from 1 to n) is provided with: a k-th sampling pipe adapted to get exhaust gas or diluted exhaust gas resulting from dilution in a dilution flow path at a (k−1)-th stage; a k-th diluter adapted to dilute with dilution air the exhaust gas or the diluted exhaust gas got through the k-th sampling pipe; a k-th dilution air flow rate control mechanism adapted to control a flow rate of the dilution air flowing into the k-th diluter; and a k-th diluted exhaust gas flow rate control mechanism adapted to control a flow rate of diluted exhaust gas flowing out of the k-th diluter. In addition, the exhaust gas dilution method includes a step of, in the dilution flow paths at the respective stages, controlling flow rates of the exhaust gas and the diluted exhaust gases got through corresponding sampling pipes by changing the flow rate of the dilution air flowing into the n-th diluter through the dilution air flow rate control mechanism at the n-th stage as a final stage.

Such configurations make it possible to, for example, in the case of changing a dilution ratio, only by changing the amount of the dilution air flowing into the n-th diluter through the dilution air flow rate control mechanism at the n-th stage as the final stage, conjunctively control the flow rates of the exhaust gas and the diluted exhaust gases got in the dilution flow paths at the respective stages, and therefore dilution ratios in the dilution flow paths at the respective stages can be simultaneously changed only by performing change work or adjustment work in the dilution flow path at the n-th stage one time. Accordingly, a mechanism or the like for adjusting the amount of the exhaust gas or diluted exhaust gas got in a dilution flow path at each stage, which has been required in the past, can be omitted to simplify the entire system.

Also, only by controlling the n-th dilution air flow rate control mechanism, for example, the flow rates of the exhaust gas and the diluted exhaust gases got at the respective stages can be made uniform, and therefore the dilution ratios in the dilution flow paths at the respective stages can be made uniform. This makes it possible to prevent a dilution ratio in a specific dilution flow path from increasing too much, and therefore a flow rate error in each dilution flow path is unlikely to affect a corresponding dilution ratio. As a result, even in the case of desiring to achieve a large dilution ratio as a whole, accuracy can be made higher than before.

In order to make it possible to accurately achieve a large dilution ratio as a whole by making it easier to uniform the dilution ratios in the dilution flow paths at the respective stages, and making a flow rate error unlikely to affect a corresponding dilution ratio, it is only necessary to perform the control such that in the dilution flow paths at the respective stages, all the flow rates of the exhaust gas and the diluted exhaust gases got through the corresponding sampling pipes are made equal to substantially the same flow rate.

In order to make the flow rates of the exhaust gas and the diluted exhaust gases got in the respective flow paths equal to accurately the same value, and make the dilution ratios in the respective flow paths equal to substantially the same value, the exhaust gas sampling apparatus is only required to be configured such that given that a dilution ratio determined by the n-th diluter in the dilution flow path at the n-th stage as the final stage is R, the dilution ratios determined by the diluters in the dilution flow paths at the respective stages other than the n-th stage as the final stage are made substantially equal to (R+1).

Note that "the dilution ratios determined by the diluters in the dilution flow paths at the respective stages other than the n-th stage as the final stage are made substantially equal to (R+1)" refers to a concept including not only the case where the dilution ratios in the dilution flow paths at the respective stages other than the n-th stage are uniformly accurately equal to (R+1), but the case where the dilution ratios are uniform within a predetermined tolerance range. For example, it is only necessary that the dilution ratios in the dilution flow paths at the stages other than the n-th stage fall within the range of plus/minus 20% with reference to (R+1).

In such a configuration, in particular, in the case where the dilution ratio R is large, the dilution ratios in the dilution flow paths at the stages other than the n-th stage as the final stage are uniformly equal to (R+1) or uniform within the predetermined tolerance range, and also have substantially the same value as that of the dilution ratio R in the dilution flow path at the n-th stage as the final stage, and therefore the dilution ratios in all the dilution flow paths can be made substantially uniform.

For this reason, the flow rate of dilution air flowing into each dilution flow path and the flow rate of the exhaust gas or diluted exhaust gas flowing into that dilution flow path can be made equal to substantially the same flow rate. As a result, a large dilution cannot be made only in some dilution flow path, and therefore the effect of a flow rate error on a corresponding dilution ratio can be minimized. Accordingly, the accuracy of the dilution ratio as the whole of the exhaust gas sampling apparatus can be maximized.

In order to make it possible to make the dilution ratios in the dilution flow paths at the stages other than the n-th stage uniformly accurately equal to (R+1) where R is the dilution ratio in the dilution flow path at the n-th stage as the final stage, and accurately achieve a large dilution ratio as the whole of the exhaust gas sampling apparatus, the exhaust gas sampling apparatus is only required to be configured such that the flow rates of the dilution air flowing into the diluters in the dilution flow paths at the respective stages other than the n-th stage as the final stage, and the flow rates of the diluted exhaust gas flowing out of the diluters through corresponding diluted exhaust gas flow rate control mechanisms in all the dilution flow paths are made equal to substantially the same flow rate.

Note that the term "substantially" here also includes a predetermined tolerance range, and means that the flow rates of the dilution air at the respective stages other than the n-th stage and the flow rates of the diluted exhaust gas at all the stages are uniform within the range of plus/minus 20%.

In such a configuration, when focusing on one dilution flow path at a stage other than the n-th stage, the flow rate of dilution air and the flow rate of diluted exhaust gas are balanced, and therefore the flow rate of diluted exhaust gas flowing in from a dilution flow path at a previous stage, and the flow rate of diluted exhaust gas flowing into a dilution flow path at a following stage are the same. That is, the flow rate of the diluted exhaust gas got through the n-th sampling pipe at the n-th stage as the final stage, and the flow rate of the exhaust gas or diluted exhaust gas got through a sampling pipe in a dilution flow path at a stage other than the n-th stage are substantially the same. The flow rate of the diluted exhaust gas got in the dilution flow path at the n-th stage as the final stage from the (n−1)-th stage is determined by the difference between the diluted exhaust gas flow rate determined by the n-th diluted exhaust gas flow rate control mechanism and the dilution air flow rate determined by the n-th dilution air flow rate control mechanism.

These make it possible to uniformly change the flow rates of the diluted exhaust gases got in the dilution flow paths at the stages other than the n-th stage and further uniformly change the dilution ratios only by changing the one dilution air flow rate determined by the n-th dilution air flow rate control mechanism.

That is, even in the case where the exhaust gas sampling apparatus includes the many flow rate control mechanisms, only by adjusting the dilution air flow rate determined by the n-th dilution air flow rate control mechanism at the n-th stage, the dilution ratios at the respective stages can be changed to another dilution ratio while being made uniformly equal to substantially the same value. For this reason, even though the number of flow rates to be adjusted is only one, the exhaust gas sampling apparatus of the present invention can accurately dilute raw exhaust gas at any dilution ratio.

In order to simplify the configuration of the exhaust gas sampling apparatus, and at the same time, make it easier to uniform the flow rates of the inflow dilution air and the accuracies of the flow rates in the dilution flow paths at the respective stages other than the n-th stage, and also increase the accuracies of the dilution ratios in the respective dilution flow paths, it is only necessary that the dilution air flow rate control mechanisms in the dilution flow paths at the respective stages other than the n-th stage as the final stage are configured such that the flow rates of the dilution air flowing into corresponding diluters are made equal to substantially the same flow rate.

Note that "the dilution air flow rate control mechanisms are configured such that the flow rates of the dilution air flowing into corresponding diluters are made equal to substantially the same flow rate" is a concept including not only the case where the flow rates of the dilution air flowing into the respective diluters are uniformly equal to accurately the same value but also the case where the flow rates are uniform within the range of plus/minus 20% with reference to a reference dilution air flow rate.

In order to make it possible to, in the respective dilution flow paths, uniform the flow rates of the exhaust and the diluted exhaust gases got through corresponding sampling pipes, and standardize components constituting the exhaust gas sampling apparatus to further simplify the configuration, it is only necessary that the diluted exhaust gas flow rate control mechanisms in the dilution flow paths at the stages other than the n-th stage as the final stage are configured such that the flow rates of the diluted exhaust gases flowing out of corresponding diluters through the diluted exhaust gas flow rate control mechanisms are made equal to substantially the same flow rate.

Note that "the diluted exhaust gas flow rate control mechanisms are configured such that the flow rates of the diluted exhaust gases flowing out of corresponding diluters through the diluted exhaust gas flow rate control mechanisms are made equal to substantially the same flow rate" is a concept including not only the case where the flow rates of the diluted exhaust gases flowing out of the corresponding diluters are uniformly equal to accurately the same value but the case where the flow rates are uniform within the range of plus/minus 20% with reference to a reference diluted exhaust gas flow rate.

In order to make it possible to accurately perform measurement such as PM measurement using diluted exhaust gas resulting from making a dilution at a large dilution ratio, it is only necessary that the dilution flow path at the n-th stage as the final stage is further provided with a filter through which the diluted exhaust gas after the dilution by the n-th diluter passes.

In order to significantly simplify the configuration of each of the dilution flow paths at the stages other than the n-th stage using the dilution ratios characterized by being changeable to any dilution ratio without securing a large flow rate variable range for each of the stages other than the n-th stage as the final stage, it is only necessary that the dilution air flow rate control mechanisms and the diluted exhaust gas flow rate control mechanisms at the respective stages other than the n-th stage as the final stage are configured to be critical flow orifices or critical flow venturis, respectively.

In order to achieve a simple configuration as an exhaust gas sampling apparatus, and at the same time, make it possible to change the dilution ratios at the respective stages to any value while making the dilution ratios substantially uniform, it is only necessary that only the n-th dilution air flow rate control mechanism at the n-th stage as the final stage is configured to be able to change the flow rate to control, and the flow rates to be controlled by the dilution air flow rate control mechanisms at the respective stages other than the n-th stage as the final stage and by the diluted exhaust gas flow rate control mechanisms at all the stages are fixed to one flow rate.

For example, in order to prevent the saturation of an output of the amount or concentration of particulate matter including PM contained in exhaust gas from an analyzer, and at the same time, make it possible to accurately perform measurement, it is only necessary to use an exhaust gas analysis system including: the exhaust gas sampling apparatus according to the present invention; and an analyzer adapted to introduce the diluted exhaust gas resulting from the dilution with the dilution air controlled by the dilution air flow rate control mechanism at the n-th stage as the final stage, and analyze the diluted exhaust gas.

Advantageous Effects of Invention

The exhaust gas sampling apparatus of the present invention can make the dilution ratios in the dilution flow paths at the respective stages substantially the same, and make it difficult for a flow rate error caused by a flow rate control mechanism provided in each of the dilution flow paths to affect a corresponding dilution ratio. For this reason, even in the case of dilute the exhaust gas at a large dilution ratio, the diluted exhaust gas resulting from the dilution made with a desired accuracy at the n-stage as the final stage can be easily obtained. Further, since the dilution ratios at the respective stages are made uniform, a flow rate control mechanism provided in each of the dilution flow paths is not required to have such a large variable flow rate range, and only a simple configuration mechanism such as a critical flow rate orifice or critical flow rate venturi capable of only controlling a fixed flow rate can be used as a standardized mechanism. As a result, the configuration of the whole of the exhaust gas sampling apparatus can be significantly simplified.

DESCRIPTION OF EMBODIMENTS

An exhaust gas analysis system 200 and an exhaust gas sampling apparatus 100 according to one embodiment of the present invention will be described with reference to FIGS. 1 and 2.

Figure 1:
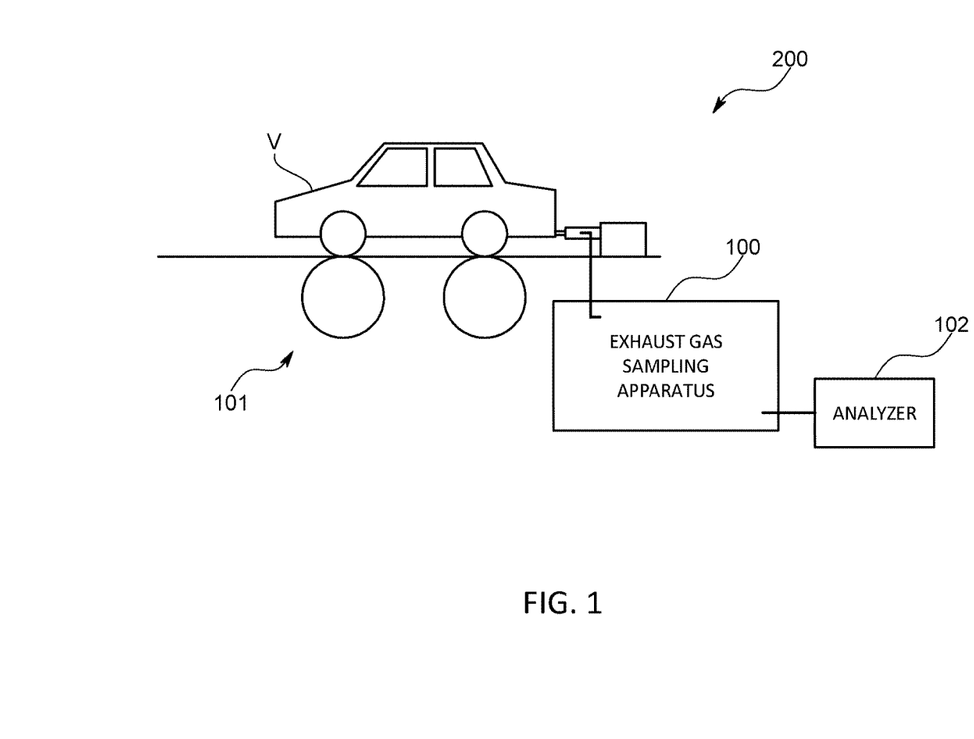
FIG. 1 is a schematic diagram illustrating an exhaust gas sampling apparatus and an exhaust gas analysis system according to one embodiment of the present invention.

The exhaust gas sampling apparatus 100 according to the present embodiment is one that as illustrated in FIG. 1, constitutes part of the exhaust gas analysis system 200 adapted to measure the amount of particulate matter (hereinafter also referred to as PM) having a predetermined particle size contained in exhaust gas. More specifically, from the side surface of an attachment pipe attached to a tail pipe of a vehicle V making a test run on a chassis dynamometer 101, a sampling pipe S of the exhaust gas sampling apparatus 100 is inserted into the attachment pipe. In addition, part of the raw exhaust gas discharged from the vehicle V is collected through the sampling pipe S, and diluted to a predetermined concentration by the exhaust gas sampling apparatus 100. The diluted exhaust gas resulting from the dilution by the exhaust gas sampling apparatus 100 is introduced into an analyzer 102 to analyze the exhaust gas. The analyzer 102 in the present embodiment is one adapted to measure the amount of particulate matter, but may be configured to measure the amounts or concentrations of other components such as $NO_x$, CO, $CO_2$, and THC.

Figure 2:
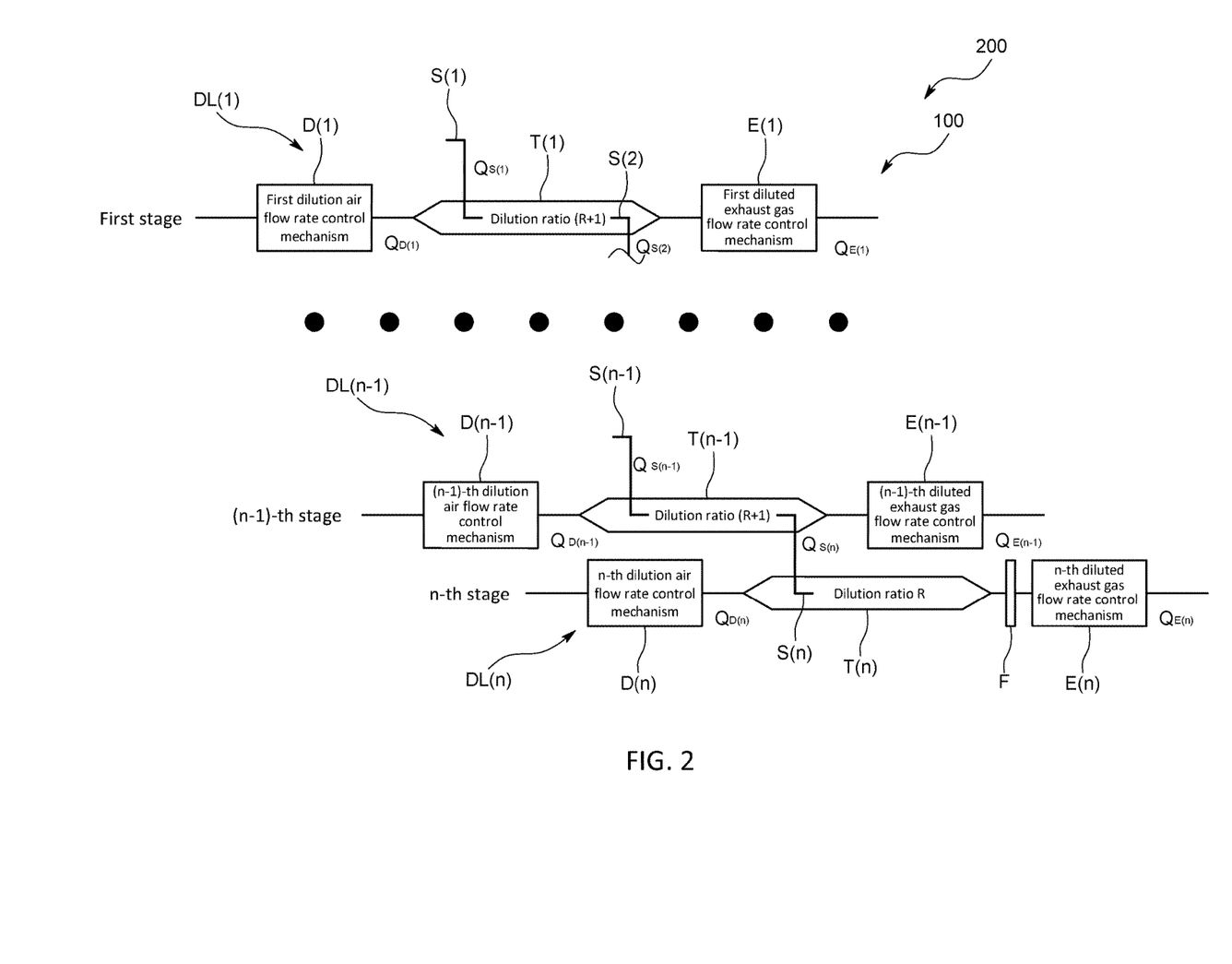
FIG. 2 is a schematic diagram illustrating the details of the exhaust gas sampling apparatus according to the same embodiment.

As illustrated in FIG. 2, the exhaust gas sampling apparatus 100 is configured to dilute the exhaust gas in a multistage manner to a concentration appropriate for measuring the amount of the PM contained in the exhaust gas. That is, the exhaust gas sampling apparatus 100 has an n-stage dilution flow path DL (n is a natural number equal to or more than 2), and is configured to dilute the exhaust gas in stages by repeating dilution of the exhaust gas or diluted exhaust gas and flow separation of the diluted exhaust gas through the respective dilution flow paths DL.

The respective dilution flow paths DL have substantially the same configuration. That is, a dilution flow path DL at a k-th stage (k is a natural number from 1 to n) is provided with: a k-th sampling pipe S adapted to get the exhaust gas or diluted exhaust gas; a k-th diluter T adapted to dilute with dilution air the exhaust gas or the diluted exhaust gas got through the k-th sampling pipe S; a k-th dilution air flow rate control mechanism D adapted to control the flow rate of the dilution air flowing into the k-th diluter T; and a k-th diluted exhaust gas flow rate control mechanism E adapted to control the flow rate of the diluted exhaust gas flowing out of the k-th diluter T. Note that in the case where components at the respective stages are easier to understand when described discriminatingly in the following description, the components at the k-th stage are represented by giving the number denoting the stage to the symbols, like DL(k), D(k), S(k), and T(k).

The first sampling pipe S(1) in the dilution flow path DL at the first stage is intended to get the exhaust gas, and a k-th sampling pipe S(k) in a dilution flow path DL(k) at a k-th stage other than the first stage is configured to get diluted exhaust gas resulting from dilution in a dilution flow path DL(k−1) at a (k−1)-th stage.

The diluter T is a tubular-shaped dilution tunnel, and from an upstream end thereof, the dilution air having passed through the dilution air flow rate control mechanism D flows in, whereas a downstream end thereof is connected to the diluted exhaust gas flow rate control mechanism E. On the upstream side inside the diluter T, a downstream end of the sampling pipe S is opened to allow the exhaust gas or the diluted exhaust gas got from the dilution flow path DL at the previous stage to flow in. In addition, in a dilution flow path DL at a stage other than the n-th stage as the final stage, on the downstream side inside a diluter T, the upstream end of a sampling pipe S constituting a dilution flow path DL at the next stage is opened to allow part of diluted exhaust gas to separately flow to the next dilution flow path DL. The rest of the diluted exhaust gas, which does not separately flow to the next dilution flow path DL, passes through a diluted exhaust gas flow rate control mechanism E and is discharged to the outside of the diluter T.

The dilution air flow rate control mechanisms D of the dilution flow paths DL at the stages other than the n-th stage are critical flow orifices or critical flow venturis configured to flow the dilution air at substantially the same flow rate. On the other hand, the dilution air flow rate control mechanism D(n) of the dilution flow path DL(n) at the n-th stage is configured to be able to appropriately change the flow rate of the dilution air.

Also, in the present embodiment, the diluted exhaust gas flow rate control mechanisms E of all the dilution flow paths DL are critical flow orifices or critical flow venturis configured to flow corresponding exhaust gases at substantially the same flow rate. In addition, each of the diluted exhaust gas flow rate control mechanisms E is connected downstream thereof to an unillustrated suction source such as a pump.

Further, in the dilution flow path DL(n) at the n-th stage as the final stage, a filter F through which the diluted exhaust gas passes is provided between the downstream end of the diluter T(n) and the diluted exhaust gas flow rate control mechanism E(n). The filter F collects PM contained in the diluted exhaust gas, and the content of the PM is measured by measuring the blackness of the filter F.

Next, the flow rate of gas flowing through each dilution flow path DL will be described in the following order: the flow rate of the gas flowing through the dilution flow path DL at the n-th stage as the final stage, and the flow rate of gas flowing through each of the dilution flow paths DL at the stages other than the n-th stage.

Since in the dilution flow path DL(n) at the n-th stage, the diluted exhaust gas is entirely discharged outside from the n-th diluter T(n) through the n-th diluted exhaust gas flow rate control mechanism E(n) without flow separation, the difference in flow rate between an outflow diluted exhaust gas flow rate $Q_{E(n)}$ controlled by the n-th diluted exhaust gas flow rate control mechanism E(n) and an inflow dilution air flow rate $Q_{D(n)}$ controlled by the n-th dilution air flow rate control mechanism D(n) is equal to the flow rate $Q_{S(n)}$ of diluted exhaust gas got from the dilution flow path DL(n−1) at the (n−1)-th stage through the n-th sampling pipe S(n).

That is, the relationship among them can be represented as $$Q_{S(n)} = Q_{E(n)} - Q_{D(n)} \quad (1)$$

Also, a dilution ratio R in the dilution flow path DL at the n-th stage can be represented from the definition thereof as $$R = (Q_{S(n)} + Q_{D(n)})/Q_{S(n)} = Q_{E(n)}/Q_{S(n)}. \quad (2)$$

The flow rate QE(n) of the diluted exhaust gas passing through the n-th diluted exhaust gas flow rate control mechanism E(n) is set so as to meet regulations such as emissions measurement regulations provided in US. In the present embodiment, the flow rate $Q_E$ is set to a flow rate determined as a flow rate at which the diluted exhaust gas should be passed through the filter F in order to measure the PM.

Next, the flow rate of gas flowing through the dilution flow path DL(k) at the k-th stage other than the n-th stage will be described.

Given that the flow rate of the dilution air controlled by the k-th dilution air flow rate control mechanism D is $Q_{D(k)}$, the flow rate of the exhaust gas or the diluted exhaust gas got from the dilution flow path DL(k−1) at the (k−1)-th stage through the k-th sampling pipe S(k) is $Q_{S(k)}$, the flow rate of the diluted exhaust gas separately flowed through the (k+1)-th sampling pipe S(k+1) is $Q_{S(k+1)}$, and the flow rate of the diluted exhaust gas discharged outside through the k-th diluted exhaust gas flow rate control mechanism E(k) is QE(k), since the flow rates of the diluted exhaust gases flowing into and flowing out of the k-th diluter T(k) are balanced, the relationship among the flow rates can be represented as follows.

$$Q_{D(k)} + Q_{S(k)} = Q_{S(k+1)} + Q_{E(k)} \quad (3)$$

Also, given that a dilution ratio in the dilution flow path DL(k) at the k-th stage is X(k), the dilution ratio X(k) can be represented from the definition of a dilution ratio as follows.

$$X(k) = (Q_{S(k)} + Q_{D(k)})/Q_{S(k)} \quad (4)$$

Note that in the present embodiment, each of the inflow dilution air flow rate $Q_{D(k)}$ controlled by the k-th dilution air flow rate control mechanism D(k) at the k-th stage other than the n-th stage and the outflow diluted exhaust gas flow rate $Q_{E(k)}$ controlled by the k-th diluted exhaust gas flow rate control mechanism E(k) is set to be equal to the flow rate $Q_{E(n)}$ of the diluted exhaust gas flowing out of the n-th diluted exhaust gas flow rate control mechanism E(n).

In short, in the dilution flow path DL(k) at the k-th stage other than the n-th stage, each of the dilution air flow rate $Q_{D(k)}$ and the flow rate $Q_{E(k)}$ at which the diluted exhaust gas passes through the k-th diluted exhaust gas flow rate control mechanism E(k) and flows outside is equal to $Q_{E(n)}$, and therefore Expression (3) can be modified as follows.

$$Q_{S(k)} = Q_{S(k+1)} \quad (5)$$

That is, the flow rates of the exhaust gas and the diluted exhaust gases got through all the sampling pipes S are the same, and equal to the flow rate $Q_{S(n)}$ of the diluted exhaust gas got in the dilution flow path DL(n) at the n-th stage. Note that the flow rate $Q_{S(n)}$ of the diluted exhaust gas got at the n-th stage can be adjusted by changing the inflow dilution air flow rate $Q_{D(n)}$ determined by the n-th dilution air flow rate control mechanism D(n). In addition, as can be seen from Expression (5), conjunctive control can be performed such that only by changing the flow rate $Q_{D(n)}$ of the dilution air flowing into the n-th diluter T(n), the flow rate $Q_{S(k)}$ of the exhaust gas or diluted exhaust gas got at each stage is also made equal to the flow rate $Q_{S(n)}$ of the diluted exhaust gas got at the n-th stage. In other words, the present embodiment is configured to set the dilution air flow rates $Q_{D(k)}$ at the respective stages except for the dilution air flow rate $Q_{D(n)}$ at the n-th stage and the outflow diluted exhaust gas flow rates $Q_{E(k)}$ at all the stage to the same flow rate, and thereby in the dilution flow paths DL(k) at the respective stages, control the flow rates $Q_{S(k)}$ of the exhaust gas and the diluted exhaust gases got through corresponding sampling pipes S(k) in conjunction with the flow rate $Q_{D(n)}$ of the dilution air flowing into the n-th diluter T(n) through the n-th dilution air flow rate control mechanism D(n).

As described above, since the dilution air flow rate $Q_{D(k)}$ at the k-th stage is controlled to be equal to the diluted exhaust gas flow rate $Q_{E(n)}$ at the n-th stage, the dilution ratio X in the dilution flow path DL at the k-th stage other than the n-th stage given by the flow rate expression (4) can be rewritten as follows.

$$X(k) = (Q_{S(n)} + Q_{E(n)}) / Q_{S(n)} \quad (6)$$

Further, from Expressions (2) and (6), the following expression can be derived.

$$X(k) = R + 1 \quad (7)$$

As described, in the present embodiment, by making the flow rates controlled by all the flow rate control mechanisms except for the n-th dilution air flow rate control mechanism D(n) uniformly equal to $Q_{E(n)}$, the dilution ratios in the dilution flow paths DL at the stages other than the n-th stage are made uniformly equal to (R+1).

Also, as can be seen from Expressions (1) and (2), when making the flow rate $Q_{D(n)}$ of the inflow dilution air from the n-th dilution air flow rate control mechanism D(n) slightly smaller than $Q_{E(n)}$, the dilution ratio in the dilution flow path DL(n) at the n-th stage has a sufficient large value, and therefore the dilution ratio R in the dilution flow path DL at the n-th stage, and the dilution ratios (R+1) in the dilution flow paths DL at the respective stages other than the n-th stage can be made uniformly equal to substantially the same value.

As described, the exhaust gas sampling apparatus 100 according to the present embodiment is adapted to make the flow rates controlled by the flow rate control mechanisms other than the n-th dilution air flow rate control mechanism D(n) uniformly equal to the flow rate $Q_{E(n)}$ of the diluted exhaust gas to be passed through the filter F. As a result, the exhaust gas sampling apparatus 100 can make the dilution ratios in the respective dilution flow paths DL uniformly equal to substantially the same value, and dilute the exhaust gas in stages.

In addition, since the exhaust gas or diluted exhaust gas is diluted in each dilution flow path DL at the small dilution ratio step by step, even in the case where an error occurs in the flow rate of the fluid flowing through the dilution flow path DL, the error is unlikely to affect the dilution ratio (R+1) or R in the dilution flow path DL.

Accordingly, even in the case of desiring to increase a dilution ratio Y as the whole of the exhaust gas sampling apparatus 100 to a large value, the dilution can be accurately made.

Also, in the case of desiring to change the dilution ratio Y as the whole of the exhaust gas sampling apparatus 100 to another value, only by changing the dilution air flow rate $Q_{D(n)}$ controlled by the n-th dilution air flow rate control mechanism D(n), the dilution ratios in the respective dilution flow paths DL(k) can be automatically made uniform. As a result, in the case of desiring to change a dilution ratio, in the past, a flow rate set in a flow rate control mechanism provided in each dilution flow path DL has been changed, whereas the exhaust gas sampling apparatus 100 according to the present embodiment can make the dilution ratios in the respective flow paths DL uniform, and accurately make the dilution at a high dilution ratio as a whole only by changing the flow rate set in the one flow rate control mechanism.

Further, in the exhaust gas sampling apparatus 100 according to the present embodiment, only the n-th dilution air flow rate control mechanism D(n) is a flow rate control mechanism having a large variable flow rate range, and for the other flow rate control mechanisms, mechanisms of the same type having a fixed flow rate can be used. Accordingly, the many flow rate control mechanisms used in the exhaust gas sampling apparatus 100 can be configured as the mechanisms of the same type to simplify the system while keeping the accuracy of the dilution ratio.

Other embodiments will be described.

In the above-described embodiment, the exhaust gas sampling apparatus 100 including the n-stage dilution flow path DL is described; however, the present invention may be configured as an exhaust gas sampling apparatus 100 including a two- or more-stage dilution flow path DL. Also, the above-described embodiment is configured to measure the exhaust gas only at the n-th stage as the final stage; however, the present invention may be configured to provide an exhaust gas measuring device in a dilution flow path DL at a middle stage to measure the exhaust gas. Each of the flow rate control mechanisms is not limited to the critical flow orifice or the critical flow venturi, but may use a mechanism configured to combine a mass flow controller or a flow rate control valve, and a controller. Further, the present invention may be configured such that in a dilution flow path DL at a stage other than the n-th stage, a dilution air flow rate $Q_{D(k)}$ determined by a corresponding dilution air flow rate control mechanism D and a diluted exhaust gas flow rate $Q_{E(k)}$ determined by a corresponding diluted exhaust gas flow rate control mechanism E are set to different values, and the dilution ratios in the dilution flow paths at the stages other than the n-th stage are made uniformly equal to (R+1) where R is the dilution ratio in the dilution flow path DL(n) at the n-th stage.

In the above-described embodiment, the case where the dilution ratios in the dilution flow paths DL at the respective stages other than the n-th stage are made uniformly equal to (R+1) is described; however, the dilution ratios in the respective dilution flow paths DL may be made uniformly equal to substantially the same value. For example, even in the case where the dilution ratios are made uniform within the range of plus/minus 20% with reference to the dilution ratio (R+1), or the dilution ratios are high dilution ratios, the exhaust gas can be accurately diluted. In addition, preferably, it is only necessary to make the dilution ratios uniform within the range of plus/minus 10% or 5% with reference to the dilution ratio (R+1).

Further, the present invention may be configured to make the dilution air flow rates controlled by the respective dilution air flow rate control mechanisms D at the stages other than the n-th stage uniform within the range of plus/minus 20% with reference to a reference flow rate $Q_{DR}$. Preferably, it is only necessary to make the flow rates controlled by the respective dilution air flow rate control mechanisms D at the stages other than the n-th stage uniform within the range of plus/minus 10% or 5% with reference to the reference flow rate $Q_{DR}$.

Still further, the dilution air flow rates $Q_{D(k)}$ at the stages other than the n-th stage and the flow rates $Q_{E(k)}$ of the diluted exhaust gas discharged through corresponding diluted exhaust gas flow rate control mechanisms E are not required to have precisely the same value.

The diluted exhaust gas flow rates controlled by the respective diluted exhaust gas flow rate control mechanisms E may also be made uniform within a predetermined range with reference to a reference flow rate $Q_{ER}$. For example, is it only necessary to make the diluted exhaust gas flow rates uniform within the range of plus/minus 20% with reference to the reference flow rate $Q_{ER}$, or preferably, the present invention may be configured to make the diluted exhaust gas flow rates uniform within the range of plus/minus 10% or 5% with reference to the reference flow rate $Q_{ER}$.

Figure 3:
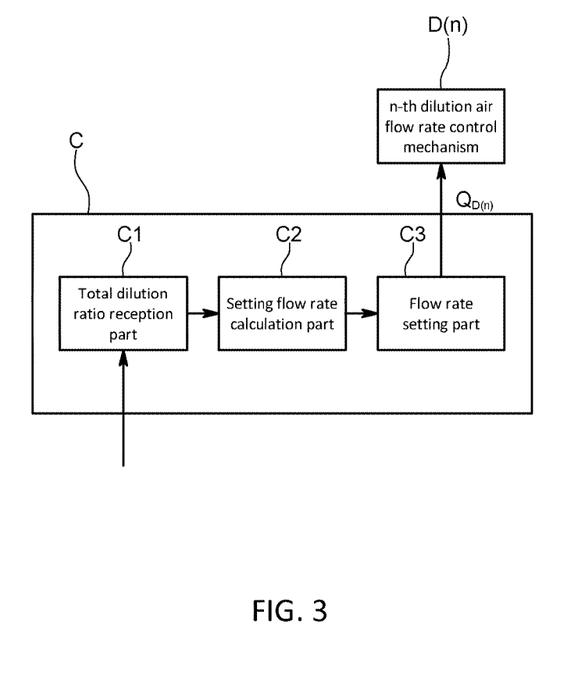
FIG. 3 is a functional block diagram illustrating the configuration of a control part of an exhaust gas sampling apparatus according to another embodiment of the present invention.

In addition, as illustrated in FIG. 3, the exhaust gas sampling apparatus 100 may further include a control part C adapted to receive the dilution ratio Y to be achieved as a whole, and change a flow rate set in the n-th dilution air flow rate control mechanism D(n) in order to achieve the dilution ratio Y.

The control part C is constituted by a computer including a CPU, memory, A/D and D/A converters, input/output means, and the like, and functions as at least a total dilution ratio reception part C1, a setting flow rate calculation part C2, and a flow rate setting part C3.

The total dilution ratio reception part C1 is one that receives the dilution ratio Y to be achieved as the whole of the exhaust gas sampling apparatus 100 through some means such as user's input, and outputs a value of the dilution ratio Y to the setting flow rate calculation part C2.

The setting flow rate calculation part C2 is one that on the basis of the received total dilution ratio Y, calculates the setting flow rate to be set in the n-th dilution air flow rate control mechanism D(n). As described in the above embodiment, given that the dilution ratio in the dilution flow path DL at the n-th stage is R, the dilution ratios in the dilution flow paths DL at the stages other than the n-th stage are (R+1), and therefore the exhaust gas dilution ratio Y as the whole of the exhaust gas sampling apparatus 100 is Y=R (R+1)$^{n-1}$, or if R is sufficiently large, can be Y≈R$^n$ as an approximate value. The setting flow rate calculation part C2 calculates the dilution ratio R at the n-th stage on the basis of any of these expressions. Further, since the flow rate $Q_{E(n)}$ of the diluted exhaust gas to be flowed to the filter F is predetermined in accordance with test regulations, the setting flow rate calculation part C2 calculates the required dilution air flow rate $Q_{D(n)}$ at the n-th stage from the calculated dilution ratio R and the flow rate $Q_{E(n)}$, and determines a value of the calculated dilution air flow rate $Q_{D(n)}$ as the setting flow rate.

The flow rate setting part C3 sets $Q_{D(n)}$, which has been calculated in the setting flow rate calculation part C2, in the n-th dilution air flow rate control mechanism D as a target value. Note that the flow rate setting part C3 is configured to change the setting flow rate to be set only in the n-th dilution air flow rate control mechanism among the many flow rate control mechanisms.

Such a configuration as described above makes it possible to activate the exhaust gas sampling apparatus 100 so as to automatically and most accuracy make the dilution on the basis of the total dilution ratio Y inputted by a user.

Note that the present invention is not limited to any of the above-described embodiments, but may include various modifications and combinations of the embodiments.

REFERENCE SIGNS LIST

200: Exhaust gas analysis system
100: Exhaust gas sampling apparatus
D(k): Dilution air flow rate control mechanism
S(k): Sampling pipe
T(k): Diluter (dilution tunnel)
E(k): Diluted exhaust gas flow rate control mechanism
C: Control part
C1: Total dilution ratio reception part
C2: Setting flow rate calculation part
C3: Flow rate setting part

What is claimed is:

1. An exhaust gas sampling apparatus comprising:
a plurality of sequential dilution flow paths each provided with
 a sampling pipe adapted to receive exhaust gas or diluted exhaust gas resulting from dilution in an immediately preceding one of the dilution flow paths,
 a diluter adapted to dilute with dilution air the exhaust gas or the diluted exhaust gas from the sampling pipe,
 a dilution air flow rate control mechanism adapted to control a flow rate of the dilution air flowing into the diluter, and
 a diluted exhaust gas flow rate control mechanism adapted to control a flow rate of diluted exhaust gas flowing out of the diluter; and
the exhaust gas sampling apparatus being configured such that, in the dilution, flow rates of the exhaust gas and the diluted exhaust gas are controlled in conjunction with the flow rate of the dilution air flowing into the diluter of a final one of the dilution flow path.

2. The exhaust gas sampling apparatus according to claim 1, wherein
the exhaust gas sampling apparatus is further configured such that, in the dilution flow paths, the flow rates of the exhaust gas and the diluted exhaust gas are made substantially same.

3. The exhaust gas sampling apparatus according to claim 1, wherein
the exhaust gas sampling apparatus is further configured such that, responsive to a dilution ratio determined by the diluter in the final one of the dilution flow paths being R, dilution ratios determined by the diluters in other of the dilution flow paths are made substantially equal to (R+1).

4. The exhaust gas sampling apparatus according to claim 1, where
the exhaust gas sampling apparatus is further configured such that the flow rates of the dilution air flowing into the diluters in the dilution flow paths other than the final one of the dilution flow path, and the flow rates of the diluted exhaust gas flowing out of the diluters in all the dilution flow paths are made substantially same.

5. The exhaust gas sampling apparatus according to claim 1, wherein
the dilution air flow rate control mechanisms in the dilution flow paths other than the final one of the dilution flow paths are configured such that the flow rates of the dilution air flowing into the diluters in the dilution flow paths other than the final one of the dilution flow paths are made substantially same.

6. The exhaust gas sampling apparatus according to claim 1, wherein
the diluted exhaust gas flow rate control mechanisms in the dilution flow paths other than the final one of the dilution flow paths are configured such that the flow rates of the diluted exhaust gas flowing out of the diluters in the dilution flow paths other than the final one of the dilution flow paths are made substantially same.

7. The exhaust gas sampling apparatus according to claim 1, wherein
the final one of the dilution flow path is further provided with a filter through which the diluted exhaust gas after the dilution by the diluter of the final one of the dilution flow paths passes.

8. The exhaust gas sampling apparatus according to claim 1, wherein
the dilution air flow rate control mechanisms and the diluted exhaust gas flow rate control mechanisms in the dilution flow paths other than the final one of the dilution flow paths are configured to be critical flow orifices or critical flow venturis, respectively.

9. The exhaust gas sampling apparatus according to claim 1, wherein
only the dilution air flow rate control mechanism in the final one of the dilution flow paths is configured to change the flow rate of the dilution air flowing into the diluter of the final one of the dilution flow paths, and
the flow rates to be controlled by the dilution air flow rate control mechanisms in other than the final one of the dilution flow paths and by the diluted exhaust gas flow rate control mechanisms in all of the dilution flow paths are fixed to one flow rate.

10. An exhaust gas analysis system comprising:
the exhaust gas sampling apparatus according to claim 1; and
an analyzer adapted to introduce the diluted exhaust gas resulting from the dilution with the dilution air controlled by the dilution air flow rate control mechanism in the final one of the dilution flow paths and to analyze the diluted exhaust gas.

11. An exhaust gas dilution method using an exhaust gas sampling apparatus comprising a plurality of sequential dilution flow paths each provided with a sampling pipe adapted to receive exhaust gas or diluted exhaust gas resulting from dilution in an immediately preceding one of the dilution flow paths, a diluter adapted to dilute with dilution air the exhaust gas or the diluted exhaust gas from the sampling pipe, a dilution air flow rate control mechanism adapted to control a flow rate of the dilution air flowing into the diluter, and a diluted exhaust gas flow rate control mechanism adapted to control a flow rate of diluted exhaust gas flowing out of the diluter, the exhaust gas dilution method comprising:
in the dilution flow paths, controlling flow rates of the exhaust gas and the diluted exhaust gas by changing the flow rate of the dilution air flowing into the diluter through the dilution air flow rate control mechanism of a final one of the dilution flow paths.

* * * * *